United States Patent
Dusch et al.

(10) Patent No.: US 6,911,329 B2
(45) Date of Patent: Jun. 28, 2005

(54) PROCESS FOR THE FERMENTATIVE PREPARATION OF D-PANTOTHENIC ACID USING CORYNEFORM BACTERIA

(75) Inventors: Nicole Dusch, Werther (DE); Hermann Thomas, Bielefeld (DE); Georg Thierbach, Bielefeld (DE)

(73) Assignee: Degussa AG, Duesseldorf (DE)

( * ) Notice: Subject to any disclaimer, the term of this patent is extended or adjusted under 35 U.S.C. 154(b) by 181 days.

(21) Appl. No.: 09/965,825

(22) Filed: Oct. 1, 2001

(65) Prior Publication Data

US 2002/0150999 A1 Oct. 17, 2002

(30) Foreign Application Priority Data

Sep. 30, 2000 (DE) .......................................... 100 48 604
Apr. 6, 2001 (DE) .......................................... 101 17 085

(51) Int. Cl.[7] .............................. C12P 7/40; C12N 1/30; C12N 9/02; C12N 15/00; C12Q 1/26
(52) U.S. Cl. .................... 435/136; 435/252.32; 435/25; 435/189; 435/148; 435/155; 435/320.1; 536/23.2
(58) Field of Search ............................. 435/252.32, 25, 435/189, 136, 148, 155, 320.1; 536/23.2

(56) References Cited

FOREIGN PATENT DOCUMENTS

| EP | 0 493 060 | 7/1992 |
|---|---|---|
| EP | 0 590 857 | 4/1994 |
| EP | 1 006 189 | 6/2000 |

OTHER PUBLICATIONS

Broun et al. , Science 282:1315–1317, 1998.*
Van de Loo et al. , Proc. Natl. Acad. Sci. 92:6743–6747, 1995.*
Seffernick et al. , J. Bacteriol. 183(8):2405–2410, 2001.*
Witkowski et al. , Biochemistry 38:11643–11650, 1999.*
J. Contiero, et al., Journal of Industrial Microbiology & Biotechnology, vol. 24, No. 6, pps. 421–430, "Effects of Mutations in Acetate Metabolism on High–Cell–Density Growth of *Escherichia coli*" (2000).

* cited by examiner

Primary Examiner—Rebecca E. Prouty
Assistant Examiner—Delia M. Ramirez
(74) Attorney, Agent, or Firm—Oblon, Spivak, McClelland, Maier & Neustadt, P.C.

(57) ABSTRACT

The invention relates to a process for preparing D-pantothenic acid using Coryneform bacteria in which the poxB gene is attenuated.

15 Claims, 2 Drawing Sheets

Figure 1: Map of the plasmid pCR2.1poxBint

SEQUENCE LISTING

<160> NUMBER OF SEQ ID NOS: 14

<210> SEQ ID NO 1
<211> LENGTH: 2160
<212> TYPE: DNA
<213> ORGANISM: Corynebacterium glutamicum
<220> FEATURE:
<221> NAME/KEY: CDS
<222> LOCATION: (327)..(2063)
<223> OTHER INFORMATION:
<221> NAME/KEY: -35_signal
<222> LOCATION: (227)..(232)
<223> OTHER INFORMATION:
<221> NAME/KEY: -10_signal
<222> LOCATION: (256)..(261)
<223> OTHER INFORMATION:

<400> SEQUENCE: 1

```
ttagaggcga ttctgtgagg tcacttttttg tggggtcggg gtctaaattt ggccagtttt     60
cgaggcgacc agacaggcgt gcccacgatg tttaaatagg cgatcggtgg gcatctgtgt    120
ttggtttcga cgggctgaaa ccaaaccaga ctgcccagca acgacggaaa tcccaaaagt    180
gggcatccct gtttggtacc gagtacccac ccgggcctga aactccctgg caggcgggcg    240
aagcgtggca acaactggaa tttaagagca caattgaagt cgcaccaagt taggcaacac    300
aatagccata acgttgagga gttcag atg gca cac agc tac gca gaa caa tta    353
                              Met Ala His Ser Tyr Ala Glu Gln Leu
                                1               5 att gac act ttg gaa gct caa ggt gtg aag cga att tat ggt ttg gtg    401
Ile Asp Thr Leu Glu Ala Gln Gly Val Lys Arg Ile Tyr Gly Leu Val
10                  15                  20                  25 ggt gac agc ctt aat ccg atc gtg gat gct gtc cgc caa tca gat att    449
Gly Asp Ser Leu Asn Pro Ile Val Asp Ala Val Arg Gln Ser Asp Ile
                30                  35                  40 gag tgg gtg cac gtt cga aat gag gaa gcg gcg gcg ttt gca gcc ggt    497
Glu Trp Val His Val Arg Asn Glu Glu Ala Ala Ala Phe Ala Ala Gly
            45                  50                  55 gcg gaa tcg ttg atc act ggg gag ctg gca gta tgt gct gct tct tgt    545
Ala Glu Ser Leu Ile Thr Gly Glu Leu Ala Val Cys Ala Ala Ser Cys
        60                  65                  70 ggt cct gga aac aca cac ctg att cag ggt ctt tat gat tcg cat cga    593
Gly Pro Gly Asn Thr His Leu Ile Gln Gly Leu Tyr Asp Ser His Arg
```

-continued

```
              75                      80                      85
aat ggt gcg aag gtg ttg gcc atc gct agc cat att ccg agt gcc cag       641
Asn Gly Ala Lys Val Leu Ala Ile Ala Ser His Ile Pro Ser Ala Gln
 90              95                     100                 105 att ggt tcg acg ttc ttc cag gaa acg cat ccg gag att ttg ttt aag       689
Ile Gly Ser Thr Phe Phe Gln Glu Thr His Pro Glu Ile Leu Phe Lys
                110                     115                 120 gaa tgc tct ggt tac tgc gag atg gtg aat ggt ggt gag cag ggt gaa       737
Glu Cys Ser Gly Tyr Cys Glu Met Val Asn Gly Gly Glu Gln Gly Glu
                    125                 130                 135 cgc att ttg cat cac gcg att cag tcc acc atg gcg ggt aaa ggt gtg       785
Arg Ile Leu His His Ala Ile Gln Ser Thr Met Ala Gly Lys Gly Val
            140                     145                 150 tcg gtg gta gtg att cct ggt gat atc gct aag gaa gac gca ggt gac       833
Ser Val Val Val Ile Pro Gly Asp Ile Ala Lys Glu Asp Ala Gly Asp
    155                     160                 165 ggt act tat tcc aat tcc act att tct tct ggc act cct gtg gtg ttc       881
Gly Thr Tyr Ser Asn Ser Thr Ile Ser Ser Gly Thr Pro Val Val Phe
170                 175                     180                 185 ccg gat cct act gag gct gca gcg ctg gtg gag gcg att aac aac gct       929
Pro Asp Pro Thr Glu Ala Ala Ala Leu Val Glu Ala Ile Asn Asn Ala
                        190                     195                 200 aag tct gtc act ttg ttc tgc ggt gcg ggc gtg aag aat gct cgc gcg       977
Lys Ser Val Thr Leu Phe Cys Gly Ala Gly Val Lys Asn Ala Arg Ala
                205                     210                 215 cag gtg ttg gag ttg gcg gag aag att aaa tca ccg atc ggg cat gcg      1025
Gln Val Leu Glu Leu Ala Glu Lys Ile Lys Ser Pro Ile Gly His Ala
            220                     225                 230 ctg ggt ggt aag cag tac atc cag cat gag aat ccg ttt gag gtc ggc      1073
Leu Gly Gly Lys Gln Tyr Ile Gln His Glu Asn Pro Phe Glu Val Gly
    235                     240                     245 atg tct ggc ctg ctt ggt tac ggc gcc tgc gtg gat gcg tcc aat gag      1121
Met Ser Gly Leu Leu Gly Tyr Gly Ala Cys Val Asp Ala Ser Asn Glu
250                     255                     260                 265 gcg gat ctg ctg att cta ttg ggt acg gat ttc cct tat tct gat ttc      1169
Ala Asp Leu Leu Ile Leu Leu Gly Thr Asp Phe Pro Tyr Ser Asp Phe
                    270                     275                 280 ctt cct aaa gac aac gtt gcc cag gtg gat atc aac ggt gcg cac att      1217
Leu Pro Lys Asp Asn Val Ala Gln Val Asp Ile Asn Gly Ala His Ile
                285                     290                 295 ggt cga cgt acc acg gtg aag tat ccg gtg acc ggt gat gtt gct gca      1265
Gly Arg Arg Thr Thr Val Lys Tyr Pro Val Thr Gly Asp Val Ala Ala
            300                     305                 310 aca atc gaa aat att ttg cct cat gtg aag gaa aaa aca gat cgt tcc      1313
Thr Ile Glu Asn Ile Leu Pro His Val Lys Glu Lys Thr Asp Arg Ser
    315                     320                 325 ttc ctt gat cgg atg ctc aag gca cac gag cgt aag ttg agc tcg gtg      1361
Phe Leu Asp Arg Met Leu Lys Ala His Glu Arg Lys Leu Ser Ser Val
330                     335                     340                 345 gta gag acg tac aca cat aac gtc gag aag cat gtg cct att cac cct      1409
Val Glu Thr Tyr Thr His Asn Val Glu Lys His Val Pro Ile His Pro
                    350                     355                 360 gaa tac gtt gcc tct att ttg aac gag ctg gcg gat aag gat gcg gtg      1457
Glu Tyr Val Ala Ser Ile Leu Asn Glu Leu Ala Asp Lys Asp Ala Val
                365                     370                 375 ttt act gtg gat acc ggc atg tgc aat gtg tgg cat gcg agg tac atc      1505
Phe Thr Val Asp Thr Gly Met Cys Asn Val Trp His Ala Arg Tyr Ile
            380                     385                 390 gag aat ccg gag gga acg cgc gac ttt gtg ggt tca ttc gcc cac ggc      1553
Glu Asn Pro Glu Gly Thr Arg Asp Phe Val Gly Ser Phe Ala His Gly
```

-continued

```
                    Glu Asn Pro Glu Gly Thr Arg Asp Phe Val Gly Ser Phe Arg His Gly
                        395                 400                 405 acg atg gct aat gcg ttg cct cat gcg att ggt gcg caa agt gtt gat        1601
Thr Met Ala Asn Ala Leu Pro His Ala Ile Gly Ala Gln Ser Val Asp
410                 415                 420                 425 cga aac cgc cag gtg atc gcg atg tgt ggc gat ggt ggt ttg ggc atg        1649
Arg Asn Arg Gln Val Ile Ala Met Cys Gly Asp Gly Gly Leu Gly Met
                430                 435                 440 ctg ctg ggt gag ctt ctg acc gtt aag ctg cac caa ctt ccg ctg aag        1697
Leu Leu Gly Glu Leu Leu Thr Val Lys Leu His Gln Leu Pro Leu Lys
            445                 450                 455 gct gtg gtg ttt aac aac agt tct ttg ggc atg gtg aag ttg gag atg        1745
Ala Val Val Phe Asn Asn Ser Ser Leu Gly Met Val Lys Leu Glu Met
        460                 465                 470 ctc gtg gag gga cag cca gaa ttt ggt act gac cat gag gaa gtg aat        1793
Leu Val Glu Gly Gln Pro Glu Phe Gly Thr Asp His Glu Glu Val Asn
    475                 480                 485 ttc gca gag att gcg gcg gct gcg ggt atc aaa tcg gta cgc atc acc        1841
Phe Ala Glu Ile Ala Ala Ala Ala Gly Ile Lys Ser Val Arg Ile Thr
490                 495                 500                 505 gat ccg aag aaa gtt cgc gag cag cta gct gag gca ttg gca tat cct        1889
Asp Pro Lys Lys Val Arg Glu Gln Leu Ala Glu Ala Leu Ala Tyr Pro
                510                 515                 520 gga cct gta ctg atc gat atc gtc acg gat cct aat gcg ctg tcg atc        1937
Gly Pro Val Leu Ile Asp Ile Val Thr Asp Pro Asn Ala Leu Ser Ile
                525                 530                 535 cca cca acc atc acg tgg gaa cag gtc atg gga ttc agc aag gcg gcc        1985
Pro Pro Thr Ile Thr Trp Glu Gln Val Met Gly Phe Ser Lys Ala Ala
            540                 545                 550 acc cga acc gtc ttt ggt gga gga gta gga gcg atg atc gat ctg gcc        2033
Thr Arg Thr Val Phe Gly Gly Gly Val Gly Ala Met Ile Asp Leu Ala
        555                 560                 565 cgt tcg aac ata agg aat att cct act cca tgatgattga tacacctgct          2083
Arg Ser Asn Ile Arg Asn Ile Pro Thr Pro
570                 575 gttctcattg accgcgagcg cttaactgcc aacatttcca ggatggcagc tcacgccggt      2143
gcccatgaga ttgccct                                                     2160

<210> SEQ ID NO 2
<211> LENGTH: 579
<212> TYPE: PRT
<213> ORGANISM: Corynebacterium glutamicum

<400> SEQUENCE: 2

Met Ala His Ser Tyr Ala Glu Gln Leu Ile Asp Thr Leu Glu Ala Gln
1               5                   10                  15

Gly Val Lys Arg Ile Tyr Gly Leu Val Gly Asp Ser Leu Asn Pro Ile
            20                  25                  30

Val Asp Ala Val Arg Gln Ser Asp Ile Glu Trp Val His Val Arg Asn
        35                  40                  45

Glu Glu Ala Ala Ala Phe Ala Ala Gly Ala Glu Ser Leu Ile Thr Gly
    50                  55                  60

Glu Leu Ala Val Cys Ala Ala Ser Cys Gly Pro Gly Asn Thr His Leu
65                  70                  75                  80

Ile Gln Gly Leu Tyr Asp Ser His Arg Asn Gly Ala Lys Val Leu Ala
                85                  90                  95

Ile Ala Ser His Ile Pro Ser Ala Gln Ile Gly Ser Thr Phe Phe Gln
            100                 105                 110
```

```
Glu Thr His Pro Glu Ile Leu Phe Lys Glu Cys Ser Gly Tyr Cys Glu
            115                 120                 125

Met Val Asn Gly Gly Glu Gln Gly Glu Arg Ile Leu His His Ala Ile
        130                 135                 140

Gln Ser Thr Met Ala Gly Lys Gly Val Ser Val Val Ile Pro Gly
145                 150                 155                 160

Asp Ile Ala Lys Glu Asp Ala Gly Asp Gly Thr Tyr Ser Asn Ser Thr
                165                 170                 175

Ile Ser Ser Gly Thr Pro Val Val Phe Pro Asp Pro Thr Glu Ala Ala
            180                 185                 190

Ala Leu Val Glu Ala Ile Asn Asn Ala Lys Ser Val Thr Leu Phe Cys
            195                 200                 205

Gly Ala Gly Val Lys Asn Ala Arg Ala Gln Val Leu Glu Leu Ala Glu
            210                 215                 220

Lys Ile Lys Ser Pro Ile Gly His Ala Leu Gly Gly Lys Gln Tyr Ile
225                 230                 235                 240

Gln His Glu Asn Pro Phe Glu Val Gly Met Ser Gly Leu Leu Gly Tyr
                245                 250                 255

Gly Ala Cys Val Asp Ala Ser Asn Glu Ala Asp Leu Leu Ile Leu Leu
                260                 265                 270

Gly Thr Asp Phe Pro Tyr Ser Asp Phe Leu Pro Lys Asp Asn Val Ala
            275                 280                 285

Gln Val Asp Ile Asn Gly Ala His Ile Gly Arg Arg Thr Thr Val Lys
            290                 295                 300

Tyr Pro Val Thr Gly Asp Val Ala Ala Thr Ile Glu Asn Ile Leu Pro
305                 310                 315                 320

His Val Lys Glu Lys Thr Asp Arg Ser Phe Leu Asp Arg Met Leu Lys
                325                 330                 335

Ala His Glu Arg Lys Leu Ser Ser Val Val Glu Thr Tyr Thr His Asn
            340                 345                 350

Val Glu Lys His Val Pro Ile His Pro Glu Tyr Val Ala Ser Ile Leu
            355                 360                 365

Asn Glu Leu Ala Asp Lys Asp Ala Val Phe Thr Val Asp Thr Gly Met
            370                 375                 380

Cys Asn Val Trp His Ala Arg Tyr Ile Glu Asn Pro Glu Gly Thr Arg
385                 390                 395                 400

Asp Phe Val Gly Ser Phe Arg His Gly Thr Met Ala Asn Ala Leu Pro
                405                 410                 415

His Ala Ile Gly Ala Gln Ser Val Asp Arg Asn Arg Gln Val Ile Ala
            420                 425                 430

Met Cys Gly Asp Gly Gly Leu Gly Met Leu Leu Gly Glu Leu Leu Thr
            435                 440                 445

Val Lys Leu His Gln Leu Pro Leu Lys Ala Val Phe Asn Asn Ser
450                 455                 460

Ser Leu Gly Met Val Lys Leu Glu Met Leu Val Glu Gly Gln Pro Glu
465                 470                 475                 480

Phe Gly Thr Asp His Glu Glu Val Asn Phe Ala Glu Ile Ala Ala Ala
                485                 490                 495

Ala Gly Ile Lys Ser Val Arg Ile Thr Asp Pro Lys Lys Val Arg Glu
            500                 505                 510

Gln Leu Ala Glu Ala Leu Ala Tyr Pro Gly Pro Val Leu Ile Asp Ile
            515                 520                 525
```

-continued

```
Val Thr Asp Pro Asn Ala Leu Ser Ile Pro Pro Thr Ile Thr Trp Glu
    530                 535                 540

Gln Val Met Gly Phe Ser Lys Ala Ala Thr Arg Thr Val Phe Gly Gly
545                 550                 555                 560

Gly Val Gly Ala Met Ile Asp Leu Ala Arg Ser Asn Ile Arg Asn Ile
                565                 570                 575

Pro Thr Pro

<210> SEQ ID NO 3
<211> LENGTH: 875
<212> TYPE: DNA
<213> ORGANISM: Corynebacterium glutamicum

<400> SEQUENCE: 3
tgcgagatgg tgaatggtgg tgagcagggt gaacgcattt tgcatcacgc gattcagtcc      60
accatggcgg gtaaaggtgt gtcggtggta gtgattcctg gtgatatcgc taaggaagac     120
gcaggtgacg gtacttattc caattccact atttcttctg cactcctgt ggtgttcccg      180 gatcctactg aggctgcagc gctggtggag gcgattaaca acgctaagtc tgtcactttg     240
ttctgcggtg cgggcgtgaa gaatgctcgc gcgcaggtgt tggagttggc ggagaagatt     300
aaatcaccga tcgggcatgc gctgggtggt aagcagtaca tccagcatga aatccgttt      360 gaggtcggca tgtctggcct gcttggttac ggcgcctgcg tggatgcgtc caatgaggcg     420
gatctgctga ttctattggg tacggatttc ccttattctg atttccttcc taagacaac      480 gttgcccagg tggatatcaa cggtgcgcac attggtcgac gtaccacggt gaagtatccg     540
gtgaccggtg atgttgctgc aacaatcgaa atatttgc ctcatgtgaa ggaaaaaaca       600
gatcgttcct tccttgatcg gatgctcaag gcacacgagc gtaagttgag ctcggtggta     660
gagacgtaca cacataacgt cgagaagcat gtgcctattc accctgaata cgttgcctct     720
attttgaacg agctggcgga taaggatgcg gtgtttactg tggataccgg catgtgcaat     780
gtgtggcatg cgaggtacat cgagaatccg gagggaacgc gcgactttgt gggttcattc     840
cgccacggca cgatggctaa tgcgttgcct catgc                                875

<210> SEQ ID NO 4
<211> LENGTH: 3248
<212> TYPE: DNA
<213> ORGANISM: Corynebacterium glutamicum
<220> FEATURE:
<221> NAME/KEY: CDS
<222> LOCATION: (802)..(2538)
<223> OTHER INFORMATION:

<400> SEQUENCE: 4
gctctcgcag caacaagagc ccacgcagtt ggagcaaacg cagcaccaag tgaagcgatt      60
ccgaaaatgc tcaagcccat gaggaacatc cggcggtggc cgattttgtc acccaaagtg     120
ccggtaccca aagaaggcc cgccatgagc agggatatg cgttgatgat ccacaacgct       180
tgggtttcgg tggctgcgag ctgttcacgc agcagaggga gtgcggtgta gagaatcgag     240
ttgtctacac cgatcagaaa gagaccaccg ctgataacgg cgaggaaagc ccaacgttgg     300
gttttcgtag gcgcttgcgc ctgtaaggtt tctgaagtca tggatcgtaa ctgtaacgaa     360
tggtcggtac agttacaact cttttgttgg tgttttagac cacggcgctg tgtggcgatt     420
taagacgtcg gaaatcgtag gggactgtca gcgtgggtcg ggttctttga ggcgcttaga     480
ggcgattctg tgaggtcact ttttgtgggg tcggggtcta aatttggcca gttttcgagg     540
```

-continued

```
cgaccagaca ggcgtgccca cgatgtttaa ataggcgatc ggtgggcatc tgtgtttggt      600
ttcgacgggc tgaaaccaaa ccagactgcc cagcaacgac ggaaatccca aaagtgggca      660
tccctgtttg gtaccgagta cccacccggg cctgaaactc cctggcaggc gggcgaagcg      720
tggcaacaac tggaatttaa gagcacaatt gaagtcgcac caagttaggc aacacaatag      780
ccataacgtt gaggagttca g atg gca cac agc tac gca gaa caa tta att        831
                        Met Ala His Ser Tyr Ala Glu Gln Leu Ile
                         1               5                   10 gac act ttg gaa gct caa ggt gtg aag cga att tat ggt ttg gtg ggt         879
Asp Thr Leu Glu Ala Gln Gly Val Lys Arg Ile Tyr Gly Leu Val Gly
             15                  20                  25 gac agc ctt aat ccg atc gtg gat gct gtc cgc caa tca gat att gag         927
Asp Ser Leu Asn Pro Ile Val Asp Ala Val Arg Gln Ser Asp Ile Glu
         30                  35                  40 tgg gtg cac gtt cga aat gag gaa gcg gcg gcg ttt gca gcc ggt gcg         975
Trp Val His Val Arg Asn Glu Glu Ala Ala Ala Phe Ala Ala Gly Ala
     45                  50                  55 gaa tcg ttg atc act ggg gag ctg gca gta tgt gct gct tct tgt ggt        1023
Glu Ser Leu Ile Thr Gly Glu Leu Ala Val Cys Ala Ala Ser Cys Gly
 60                  65                  70 cct gga aac aca cac ctg att cag ggt ctt tat gat tcg cat cga aat        1071
Pro Gly Asn Thr His Leu Ile Gln Gly Leu Tyr Asp Ser His Arg Asn
 75                  80                  85                  90 ggt gcg aag gtg ttg gcc atc gct agc cat att ccg agt gcc cag att        1119
Gly Ala Lys Val Leu Ala Ile Ala Ser His Ile Pro Ser Ala Gln Ile
                 95                 100                 105 ggt tcg acg ttc ttc cag gaa acg cat ccg gag att ttg ttt aag gaa        1167
Gly Ser Thr Phe Phe Gln Glu Thr His Pro Glu Ile Leu Phe Lys Glu
             110                 115                 120 tgc tct ggt tac tgc gag atg gtg aat ggt ggt gag cag ggt gaa cgc        1215
Cys Ser Gly Tyr Cys Glu Met Val Asn Gly Gly Glu Gln Gly Glu Arg
         125                 130                 135 att ttg cat cac gcg att cag tcc acc atg gcg ggt aaa ggt gtg tcg        1263
Ile Leu His His Ala Ile Gln Ser Thr Met Ala Gly Lys Gly Val Ser
     140                 145                 150 gtg gta gtg att cct ggt gat atc gct aag gaa gac gca ggt gac ggt        1311
Val Val Val Ile Pro Gly Asp Ile Ala Lys Glu Asp Ala Gly Asp Gly
155                 160                 165                 170 act tat tcc aat tcc act att tct tct ggc act cct gtg gtg ttc ccg        1359
Thr Tyr Ser Asn Ser Thr Ile Ser Ser Gly Thr Pro Val Val Phe Pro
                 175                 180                 185 gat cct act gag gct gca gcg ctg gtg gag gcg att aac aac gct aag        1407
Asp Pro Thr Glu Ala Ala Ala Leu Val Glu Ala Ile Asn Asn Ala Lys
             190                 195                 200 tct gtc act ttg ttc tgc ggt gcg ggc gtg aag aat gct cgc gcg cag        1455
Ser Val Thr Leu Phe Cys Gly Ala Gly Val Lys Asn Ala Arg Ala Gln
         205                 210                 215 gtg ttg gag ttg gcg gag aag att aaa tca ccg atc ggg cat gcg ctg        1503
Val Leu Glu Leu Ala Glu Lys Ile Lys Ser Pro Ile Gly His Ala Leu
     220                 225                 230 ggt ggt aag cag tac atc cag cat gag aat ccg ttt gag gtc ggc atg        1551
Gly Gly Lys Gln Tyr Ile Gln His Glu Asn Pro Phe Glu Val Gly Met
235                 240                 245                 250 tct ggc ctg ctt ggt tac ggc gcc tgc gtg gat gcg tcc aat gag gcg        1599
Ser Gly Leu Leu Gly Tyr Gly Ala Cys Val Asp Ala Ser Asn Glu Ala
                 255                 260                 265 gat ctg ctg att cta ttg ggt acg gat ttc cct tat tct gat ttc ctt        1647
Asp Leu Leu Ile Leu Leu Gly Thr Asp Phe Pro Tyr Ser Asp Phe Leu
             270                 275                 280
```

```
cct aaa gac aac gtt gcc cag gtg gat atc aac ggt gcg cac att ggt    1695
Pro Lys Asp Asn Val Ala Gln Val Asp Ile Asn Gly Ala His Ile Gly
        285                 290                 295 cga cgt acc acg gtg aag tat ccg gtg acc ggt gat gtt gct gca aca    1743
Arg Arg Thr Thr Val Lys Tyr Pro Val Thr Gly Asp Val Ala Ala Thr
    300                 305                 310 atc gaa aat att ttg cct cat gtg aag gaa aaa aca gat cgt tcc ttc    1791
Ile Glu Asn Ile Leu Pro His Val Lys Glu Lys Thr Asp Arg Ser Phe
315                 320                 325                 330 ctt gat cgg atg ctc aag gca cac gag cgt aag ttg agc tcg gtg gta    1839
Leu Asp Arg Met Leu Lys Ala His Glu Arg Lys Leu Ser Ser Val Val
                335                 340                 345 gag acg tac aca cat aac gtc gag aag cat gtg cct att cac cct gaa    1887
Glu Thr Tyr Thr His Asn Val Glu Lys His Val Pro Ile His Pro Glu
            350                 355                 360 tac gtt gcc tct att ttg aac gag ctg gcg gat aag gat gcg gtg ttt    1935
Tyr Val Ala Ser Ile Leu Asn Glu Leu Ala Asp Lys Asp Ala Val Phe
        365                 370                 375 act gtg gat acc ggc atg tgc aat gtg tgg cat gcg agg tac atc gag    1983
Thr Val Asp Thr Gly Met Cys Asn Val Trp His Ala Arg Tyr Ile Glu
    380                 385                 390 aat ccg gag gga acg cgc gac ttt gtg ggt tca ttc cgc cac ggc acg    2031
Asn Pro Glu Gly Thr Arg Asp Phe Val Gly Ser Phe Arg His Gly Thr
395                 400                 405                 410 atg gct aat gcg ttg cct cat gcg att ggt gcg caa agt gtt gat cga    2079
Met Ala Asn Ala Leu Pro His Ala Ile Gly Ala Gln Ser Val Asp Arg
                415                 420                 425 aac cgc cag gtg atc gcg atg tgt ggc gat ggt ggt ttg ggc atg ctg    2127
Asn Arg Gln Val Ile Ala Met Cys Gly Asp Gly Gly Leu Gly Met Leu
            430                 435                 440 ctg ggt gag ctt ctg acc gtt aag ctg cac caa ctt ccg ctg aag gct    2175
Leu Gly Glu Leu Leu Thr Val Lys Leu His Gln Leu Pro Leu Lys Ala
        445                 450                 455 gtg gtg ttt aac aac agt tct ttg ggc atg gtg aag ttg gag atg ctc    2223
Val Val Phe Asn Asn Ser Ser Leu Gly Met Val Lys Leu Glu Met Leu
    460                 465                 470 gtg gag gga cag cca gaa ttt ggt act gac cat gag gaa gtg aat ttc    2271
Val Glu Gly Gln Pro Glu Phe Gly Thr Asp His Glu Glu Val Asn Phe
475                 480                 485                 490 gca gag att gcg gcg gct gcg ggt atc aaa tcg gta cgc atc acc gat    2319
Ala Glu Ile Ala Ala Ala Ala Gly Ile Lys Ser Val Arg Ile Thr Asp
                495                 500                 505 ccg aag aaa gtt cgc gag cag cta gct gag gca ttg gca tat cct gga    2367
Pro Lys Lys Val Arg Glu Gln Leu Ala Glu Ala Leu Ala Tyr Pro Gly
            510                 515                 520 cct gta ctg atc gat atc gtc acg gat cct aat gcg ctg tcg atc cca    2415
Pro Val Leu Ile Asp Ile Val Thr Asp Pro Asn Ala Leu Ser Ile Pro
        525                 530                 535 cca acc atc acg tgg gaa cag gtc atg gga ttc agc aag gcg gcc acc    2463
Pro Thr Ile Thr Trp Glu Gln Val Met Gly Phe Ser Lys Ala Ala Thr
    540                 545                 550 cga acc gtc ttt ggt gga gga gta gga gcg atg atc gat ctg gcc cgt    2511
Arg Thr Val Phe Gly Gly Gly Val Gly Ala Met Ile Asp Leu Ala Arg
555                 560                 565                 570 tcg aac ata agg aat att cct act cca tgatgattga tacacctgct          2558
Ser Asn Ile Arg Asn Ile Pro Thr Pro
                575 gttctcattg accgcgagcg cttaactgcc aacatttcca ggatggcagc tcacgccggt  2618
```

```
gcccatgaga ttgccctgcg tccgcatgtg aaaacgcaca aaatcattga aattgcgcag    2678
atgcaggtcg acgccggtgc ccgagggatc acctgcgcaa ccattggcga ggcggaaatt    2738
tttgccggcg caggttttac ggacatcttt attgcatatc cgctgtatct aaccgatcat    2798
gcagtgcaac gcctgaacgc gatccccgga gaaatttcca ttggcgtgga ttcggtagag    2858
atggcacagg cgacggcggg tttgcgggaa gatatcaagg ctctgattga agtggattcg    2918
ggacatcgta gaagtggagt cacggcgact gcttcagaat tgagtcagat ccgcgaggcg    2978
ctgggcagca ggtatgcagg agtgtttact tttcctgggc attcttatgg cccgggaaat    3038
ggtgagcagg cagcagctga tgagcttcag gctctaaaca acagcgtcca gcgacttgct    3098
ggcggcctga cttctggcgg ttcctcgccg tctgcgcagt ttacagacgc aatcgatgag    3158
atgcgaccag gcgtgtatgt gtttaacgat tcccagcaga tcacctcggg agcatgcact    3218
gagaagcagg tggcaatgac ggtgctgtct                                    3248
```

<210> SEQ ID NO 5
<211> LENGTH: 579
<212> TYPE: PRT
<213> ORGANISM: Corynebacterium glutamicum

<400> SEQUENCE: 5

```
Met Ala His Ser Tyr Ala Glu Gln Leu Ile Asp Thr Leu Glu Ala Gln
1               5                   10                  15

Gly Val Lys Arg Ile Tyr Gly Leu Val Gly Asp Ser Leu Asn Pro Ile
            20                  25                  30

Val Asp Ala Val Arg Gln Ser Asp Ile Glu Trp Val His Val Arg Asn
        35                  40                  45

Glu Glu Ala Ala Phe Ala Ala Gly Ala Glu Ser Leu Ile Thr Gly
    50                  55                  60

Glu Leu Ala Val Cys Ala Ala Ser Cys Gly Pro Gly Asn Thr His Leu
65                  70                  75                  80

Ile Gln Gly Leu Tyr Asp Ser His Arg Asn Gly Ala Lys Val Leu Ala
                85                  90                  95

Ile Ala Ser His Ile Pro Ser Ala Gln Ile Gly Ser Thr Phe Phe Gln
            100                 105                 110

Glu Thr His Pro Glu Ile Leu Phe Lys Glu Cys Ser Gly Tyr Cys Glu
        115                 120                 125

Met Val Asn Gly Gly Glu Gln Gly Glu Arg Ile Leu His His Ala Ile
    130                 135                 140

Gln Ser Thr Met Ala Gly Lys Gly Val Ser Val Val Ile Pro Gly
145                 150                 155                 160

Asp Ile Ala Lys Glu Asp Ala Gly Asp Gly Thr Tyr Ser Asn Ser Thr
                165                 170                 175

Ile Ser Ser Gly Thr Pro Val Val Phe Pro Asp Pro Thr Glu Ala Ala
            180                 185                 190

Ala Leu Val Glu Ala Ile Asn Asn Ala Lys Ser Val Thr Leu Phe Cys
        195                 200                 205

Gly Ala Gly Val Lys Asn Ala Arg Ala Gln Val Leu Glu Leu Ala Glu
    210                 215                 220

Lys Ile Lys Ser Pro Ile Gly His Ala Leu Gly Gly Lys Gln Tyr Ile
225                 230                 235                 240

Gln His Glu Asn Pro Phe Glu Val Gly Met Ser Gly Leu Leu Gly Tyr
                245                 250                 255

Gly Ala Cys Val Asp Ala Ser Asn Glu Ala Asp Leu Leu Ile Leu Leu
```

```
                    260                 265                 270
Gly Thr Asp Phe Pro Tyr Ser Asp Phe Leu Pro Lys Asp Asn Val Ala
            275                 280                 285
Gln Val Asp Ile Asn Gly Ala His Ile Gly Arg Arg Thr Thr Val Lys
        290                 295                 300
Tyr Pro Val Thr Gly Asp Val Ala Ala Thr Ile Glu Asn Ile Leu Pro
305                 310                 315                 320
His Val Lys Glu Lys Thr Asp Arg Ser Phe Leu Asp Arg Met Leu Lys
                325                 330                 335
Ala His Glu Arg Lys Leu Ser Ser Val Val Glu Thr Tyr Thr His Asn
            340                 345                 350
Val Glu Lys His Val Pro Ile His Pro Glu Tyr Val Ala Ser Ile Leu
        355                 360                 365
Asn Glu Leu Ala Asp Lys Asp Ala Val Phe Thr Val Asp Thr Gly Met
    370                 375                 380
Cys Asn Val Trp His Ala Arg Tyr Ile Glu Asn Pro Glu Gly Thr Arg
385                 390                 395                 400
Asp Phe Val Gly Ser Phe Arg His Gly Thr Met Ala Asn Ala Leu Pro
                405                 410                 415
His Ala Ile Gly Ala Gln Ser Val Asp Arg Asn Arg Gln Val Ile Ala
            420                 425                 430
Met Cys Gly Asp Gly Gly Leu Gly Met Leu Leu Gly Glu Leu Leu Thr
        435                 440                 445
Val Lys Leu His Gln Leu Pro Leu Lys Ala Val Val Phe Asn Asn Ser
    450                 455                 460
Ser Leu Gly Met Val Lys Leu Glu Met Leu Val Glu Gly Gln Pro Glu
465                 470                 475                 480
Phe Gly Thr Asp His Glu Glu Val Asn Phe Ala Glu Ile Ala Ala Ala
                485                 490                 495
Ala Gly Ile Lys Ser Val Arg Ile Thr Asp Pro Lys Lys Val Arg Glu
            500                 505                 510
Gln Leu Ala Glu Ala Leu Ala Tyr Pro Gly Pro Val Leu Ile Asp Ile
        515                 520                 525
Val Thr Asp Pro Asn Ala Leu Ser Ile Pro Pro Thr Ile Thr Trp Glu
    530                 535                 540
Gln Val Met Gly Phe Ser Lys Ala Ala Thr Arg Thr Val Phe Gly Gly
545                 550                 555                 560
Gly Val Gly Ala Met Ile Asp Leu Ala Arg Ser Asn Ile Arg Asn Ile
                565                 570                 575
Pro Thr Pro
```

<210> SEQ ID NO 6
<211> LENGTH: 475
<212> TYPE: DNA
<213> ORGANISM: Corynebacterium glutamicum

<400> SEQUENCE: 6

```
gctctcgcag caacaagagc ccacgcagtt ggagcaaacg cagcaccaag tgaagcgatt    60
ccgaaaatgc tcaagcccat gaggaacatc cggcggtggc cgattttgtc acccaaagtg   120
ccggtaccca aagaaggcc cgccatgagc agggatatg cgttgatgat ccacaacgct    180
tgggtttcgg tggctgcgag ctgttcacgc agcagaggga gtgcggtgta gagaatcgag   240
ttgtctacac cgatcagaaa gagaccaccg ctgataacgg cgaggaaagc ccaacgttgg   300
```

-continued

| | |
|---|---|
| gttttcgtag gcgcttgcgc ctgtaaggtt tctgaagtca tggatcgtaa ctgtaacgaa | 360 |
| tggtcggtac agttacaact cttttgttgg tgttttagac cacggcgctg tgtggcgatt | 420 |
| taagacgtcg gaaatcgtag gggactgtca gcgtgggtcg ggttctttga ggcgc | 475 |

<210> SEQ ID NO 7
<211> LENGTH: 613
<212> TYPE: DNA
<213> ORGANISM: Corynebacterium glutamicum

<400> SEQUENCE: 7

| | |
|---|---|
| gcgtccgcat gtgaaaacgc acaaaatcat tgaaattgcg cagatgcagg tcgacgccgg | 60 |
| tgcccgaggg atcacctgcg caaccattgg cgaggcggaa attttttgccg gcgcaggttt | 120 |
| tacggacatc tttattgcat atccgctgta tctaaccgat catgcagtgc aacgcctgaa | 180 |
| cgcgatcccc ggagaaattt ccattggcgt ggattcggta gagatggcac aggcgacggc | 240 |
| gggtttgcgg gaagatatca aggctctgat tgaagtggat tcgggacatc gtagaagtgg | 300 |
| agtcacggcg actgcttcag aattgagtca gatccgcgag gcgctgggca gcaggtatgc | 360 |
| aggagtgttt acttttcctg ggcattctta tggcccggga aatggtgagc aggcagcagc | 420 |
| tgatgagctt caggctctaa acaacagcgt ccagcgactt gctggcggcc tgacttctgg | 480 |
| cggttcctcg ccgtctgcgc agtttacaga cgcaatcgat gagatgcgac caggcgtgta | 540 |
| tgtgtttaac gattcccagc agatcacctc gggagcatgc actgagaagc aggtggcaat | 600 |
| gacggtgctg tct | 613 |

<210> SEQ ID NO 8
<211> LENGTH: 20
<212> TYPE: DNA
<213> ORGANISM: Artificial Sequence
<220> FEATURE:
<223> OTHER INFORMATION: synthetic DNA

<400> SEQUENCE: 8

| | |
|---|---|
| atgaggaaca tccggcggtg | 20 |

<210> SEQ ID NO 9
<211> LENGTH: 48
<212> TYPE: DNA
<213> ORGANISM: Artificial Sequence
<220> FEATURE:
<223> OTHER INFORMATION: synthetic DNA

<400> SEQUENCE: 9

| | |
|---|---|
| gagaacagca ggagtatcaa tcatcactga actcctcaac gttatggc | 48 |

<210> SEQ ID NO 10
<211> LENGTH: 26
<212> TYPE: DNA
<213> ORGANISM: Artificial Sequence
<220> FEATURE:
<223> OTHER INFORMATION: synthetic DNA

<400> SEQUENCE: 10

| | |
|---|---|
| tgatgattga tacacctgct gttctc | 26 |

<210> SEQ ID NO 11
<211> LENGTH: 20
<212> TYPE: DNA
<213> ORGANISM: Artificial Sequence
<220> FEATURE:
<223> OTHER INFORMATION: synthetic DNA

<400> SEQUENCE: 11
tcattgccac ctgcttctca                                                      20

<210> SEQ ID NO 12
<211> LENGTH: 1422
<212> TYPE: DNA
<213> ORGANISM: Corynebacterium glutamicum

<400> SEQUENCE: 12
atgaggaaca tccggcggtg gccgattttg tcacccaaag tgccggtacc caaaagaagg          60
cccgccatga gcaggggata tgcgttgatg atccacaacg cttgggtttc ggtggctgcg        120
agctgttcac gcagcagagg gagtgcggtg tagagaatcg agttgtctac accgatcaga        180
aagagaccac cgctgataac ggcgaggaaa gcccaacgtt gggttttcgt aggcgcttgc        240
gcctgtaagg tttctgaagt catggatcgt aactgtaacg aatggtcggt acagttacaa        300
ctcttttgtt ggtgttttag accacggcgc tgtgtggcga tttaagacgt cggaaatcgt        360
aggggactgt cagcgtgggt cgggttcttt gaggcgctta gaggcgattc tgtgaggtca        420
ctttttgtgg ggtcggggtc taaatttggc cagttttcga ggcgaccaga caggcgtgcc        480
cacgatgttt aaataggcga tcggtgggca tctgtgtttg gtttcgacgg gctgaaacca        540
aaccagactg cccagcaacg acggaaatcc caaaagtggg catccctgtt tggtaccgag        600
tacccacccg ggcctgaaac tccctggcag gcgggcgaag cgtggcaaca actggaattt        660
aagagcacaa ttgaagtcgc accaagttag gcaacacaat agccataaag ttgaggagtt        720
cagtgatgat tgatacacct gctgttctca ttgaccgcga gcgcttaact gccaacattt        780
ccaggatggc agctcacgcc ggtgcccatg agattgccct gcgtccgcat gtgaaaacgc        840
acaaaatcat tgaaattgcg cagatgcagg tcgacgccgg tgcccgaggg atcacctgcg        900
caaccattgg cgaggcggaa attttttgccg gcgcaggttt tacggacatc tttattgcat        960
atccgctgta tctaaccgat catgcagtgc aacgcctgaa cgcgatcccc ggagaaattt       1020
ccattggcgt ggattcggta gagatggcac aggcgacggc gggtttgcgg gaagatatca       1080
aggctctgat tgaagtggat tcgggacatc gtagaagtgg agtcacggcg actgcttcag       1140
aattgagtca gatccgcgag gcgctgggca gcaggtatgc aggagtgttt acttttcctg       1200
ggcattctta tggcccggga aatggtgagc aggcagcagc tgatgagctt caggctctaa       1260
acaacagcgt ccagcgactt gctggcggcc tgacttctgg cggttcctcg ccgtctgcgc       1320
agtttacaga cgcaatcgat gagatgcgac caggcgtgta tgtgtttaac gattcccagc       1380
agatcacctc gggagcatgc actgagaagc aggtggcaat ga                          1422

<210> SEQ ID NO 13
<211> LENGTH: 20
<212> TYPE: DNA
<213> ORGANISM: Artificial Sequence
<220> FEATURE:
<223> OTHER INFORMATION: synthetic DNA

<400> SEQUENCE: 13
tgcgagatgg tgaatggtgg                                                     20

<210> SEQ ID NO 14
<211> LENGTH: 20
<212> TYPE: DNA
<213> ORGANISM: Artificial Sequence
<220> FEATURE:

-continued

<223> OTHER INFORMATION: synthetic DNA

<400> SEQUENCE: 14
gcatgaggca acgcattagc                                                    20

PROCESS FOR THE FERMENTATIVE PREPARATION OF D-PANTOTHENIC ACID USING CORYNEFORM BACTERIA

BACKGROUND OF THE INVENTION

1. Field of the Invention

The invention relates to a process for preparing D-pantothenic acid using Coryneform bacteria in which the poxB gene is attenuated.

2. Discussion of the Background

Pantothenic acid is a vitamin of commercial importance, which is can be used in human medicine, pharmaceuticals, foodstuffs industry and particularly in animal nutrition. Pantothenic acid can be prepared by chemical synthesis, or biotechnologically by fermentation of suitable microorganisms in suitable nutrient solutions. In the chemical synthesis, DL-pantolactone is an important intermediate stage. It is prepared in a multi-stage process from formaldehyde, isobutylaldehyde and cyanide. In further process steps, the racemic mixture is separated, D-pantolactone is subjected to a condensation reaction with β-alanine, and the desired D-pantothenic acid is obtained in this way.

The advantage of the fermentative preparation by microorganisms lies in the direct formation of the desired stereoisomeric D-form, which is free from L-pantothenic acid.

Various types of bacteria, e.g. *Escherichia coli* (*E. coli*), *Arthrobacter ureafaciens*, *Corynebacterium erythrogenes*, *Brevibacterium ammoniagenes*, and also yeasts, e.g. *Debaromyces castellii*, can produce D-pantothenic acid in a nutrient solution which comprises glucose, DL-pantoic acid and β-alanine, as shown in EP-A 0 493 060. EP-A 0 493 060 further shows that in the case of *E. coli*, the formation of D-pantothenic acid is improved by amplification of pantothenic acid biosynthesis genes from *E. coli* which are contained on the plasmids pFV3 and pFV5 in a nutrient solution comprising glucose, DL-pantoic acid and β-alanine.

EP-A 0 590 857 and U.S. Pat. No. 5,518,906 describe mutants derived from *E. coli* strain IF3547, such as FV5714, FV525, FV814, FV521, FV221, FV6051 and FV5069, which carry resistances to various antimetabolites, such as salicylic acid, α-ketobutyric acid, β-hydroxyaspartic acid, O-methylthreonine and α-ketoisovaleric acid. They produce pantoic acid in a nutrient solution comprising glucose, and D-pantothenic acid in a nutrient solution comprising glucose and β-alanine. It is further shown in EP-A 0 590 857 and U.S. Pat. No. 5,518,906 that after amplification of the pantothenic acid biosynthesis genes contained on the plasmid pFV31, in the above-mentioned strains the production of D-pantoic acid in nutrient solutions comprising glucose and the production of D-pantothenic acid in a nutrient solution comprising glucose and β-alanine is improved.

Processes for the preparation of D-pantothenic acid with the aid of *Corynebacterium glutamicum* (*C. glutamicum*) are known only in some instances in the literature. Sahm and Eggeling (Applied and Environmental Microbiology 65(5), 1973–1979 (1999)) thus report on the influence of overexpression of the panB and panC genes and Dusch et al. (Applied and Environmental Microbiology 65(4), 1530–1539 (1999)) report on the influence of the panD gene on the formation of D-pantothenic acid.

However, there remains a need for improved methods of producing pantothenic acid in Coryneform bacteria. On a commercial or industrial scale even small improvements in the yield of pantothenic acid, or the efficiency of their production, are economically significant. Prior to the present invention, it was not recognized that attenuation of the poxB gene in Coryneform bacteria would improve pantothenic acid yields.

SUMMARY OF THE INVENTION

One object of the present invention, is providing a new process for producing D-pantothenic acid by culturing a Coryneform bacteria comprising an attenuated poxB gene and collecting the D-pantothenic acid produced. On embodiment of a attenuated poxB gene is the gene that has the sequence of SEQ ID NO:12.

The attenuation can be accomplished by removing part or the whole gene. For example, the sequence in SEQ ID NO:3 can be used to direct homologous recombination to delete a portion of the endogenous poxB gene shown in SEQ ID NO:1 or SEQ ID NO:4. Likewise, the poxB gene can be attenuated by employing the sequences of SEQ ID NO:6 and SEQ ID NO:7 in homologous recombination.

Another object of the present invention is to prepare D-pantothenic acid in bacteria with attenuated poxB gene and also having enhanced expression of one or more of panB gene, panC gene, and/or ilvD gene.

Another object of the present invention is to prepare Coryneform bacteria with an attenuated poxB gene.

In one embodiment the poxB gene is attenuated by eliminatation.

Other objects of the invention are isolated polynucleotides which comprise one or more of SEQ ID NOS:6, 7 and/or 12.

The above objects highlight certain aspects of the invention. Additional objects, aspects and embodiments of the invention are found in the following detailed description of the invention.

DETAILED DESCRIPTION OF THE INVENTION

Figure 1:
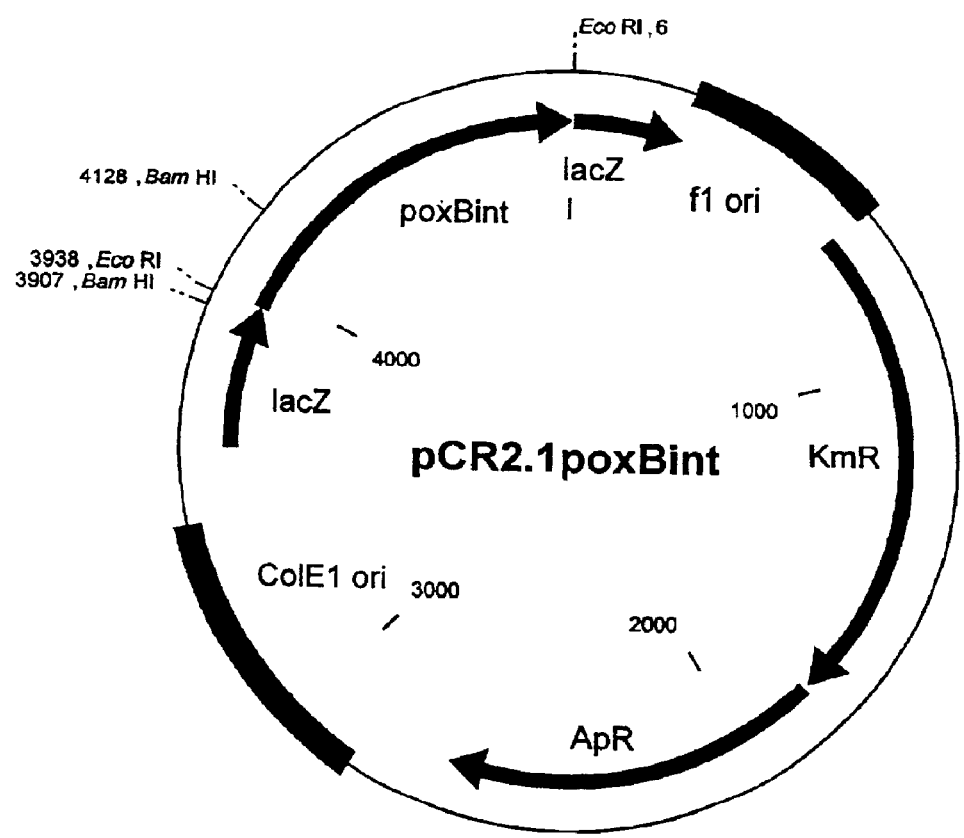
FIG. 1: Map of the plasmid pCR2.1poxBint.

Unless otherwise defined, all technical and scientific terms used herein have the same meaning as commonly understood by one of ordinary skill in the art of molecular biology. Although methods and materials similar or equivalent to those described herein can be used in the practice or testing of the present invention, suitable methods and materials are described herein. All publications, patent applications, patents, and other references mentioned herein are incorporated by reference in their entirety. In addition, the materials, methods, and examples are illustrative only and are not intended to be limiting.

Reference is made to standard textbooks of molecular biology that contain definitions and methods and means for carrying out basic techniques, encompassed by the present invention. See, for example, Sambrook et al., Molecular Cloning: A Laboratory Manual, Cold Spring Harbor Laboratory, N.Y. (1989); Current Protocols in Molecular Biology, Ausebel et al (eds.), John Wiley and Sons, Inc., N.Y. (2000) and the various references cited therein.

"D-pantothenic acid" or "pantothenic acid" or "pantothenate" as used herein mean the free acids and the salts of D-pantothenic acid, such as calcium, sodium, ammonium or potassium salts.

The invention provides a process for the fermentative preparation of D-pantothenic acid using Coryneform bacteria in which the nucleotide sequence which codes for the enzyme pyruvate oxidase (EC 1.2.2.2) (poxB gene) is attenuated.

This invention also provides a process for the fermentative preparation of D-pantothenic acid, in which the following steps are carried out:

a) fermentation of D-pantothenic acid-producing Coryneform bacteria in which at least the nucleotide sequence which codes for pyruvate oxidase (EC 1.2.2.2) (poxB) is attenuated, in particular eliminated;

b) concentration of the D-pantothenic acid in the medium or in the cells of the bacteria; and c) isolation of the D-pantothenic acid produced.

The strains employed optionally already produce D-pantothenic acid before attenuation of the poxB gene.

The term "attenuation" in this connection describes the reduction or elimination of the intracellular activity of one or more enzymes (proteins) in a microorganism which are coded by the corresponding DNA, for example by using a weak promoter or using a gene or allele which codes for a corresponding enzyme (protein) with a low activity or inactivates the corresponding gene or enzyme (protein), and optionally combining these measures.

By attenuation measures, the activity or concentration of the corresponding protein is in general reduced to 0 to 75%, 0 to 50%, 0 to 25%, 0 to 10% or 0 to 5% of the activity or concentration of the wild-type protein or of the activity or concentration of the protein in the starting microorganism.

Preferably, a Coryneform bateria with attenuated expression of the poxB gene will improve D-pantothenic acid productivity at least 1% compared to a bacteria which does not contain such an attenuated poxB gene.

The microorganisms which the present invention provides can produce D-pantothenic acid from glucose, sucrose, lactose, fructose, maltose, molasses, starch, cellulose or from glycerol and ethanol. They are representatives of Coryneform bacteria, in particular of the genus *Corynebacterium*. Of the genus *Corynebacterium*, there may be mentioned in particular the species *Corynebacterium glutamicum*, which is known among experts for its ability to produce L-amino acids.

Suitable strains of the genus *Corynebacterium*, in particular of the species *Corynebacterium glutamicum*, are, for example, the known wild-type strains

*Corynebacterium glutamicum* ATCC13032
*Corynebacterium acetoglutamicum* ATCC15806
*Corynebacterium acetoacidophilum* ATCC13870
*Corynebacterium melassecola* ATCC17965
*Corynebacterium thermoaminogenes* FERM BP-1539
*Brevibacterium flavum* ATCC14067
*Brevibacterium lactofermentum* ATCC13869 and
*Brevibacterium divaricatum* ATCC14020 and D-pantothenic acid-producing mutants prepared therefrom, such as:

*Corynebacterium glutamicum* ATCC13032ΔilvA/pEC7panBC
*Corynebacterium glutamicum* ATCC13032/pND-D2.

It has been found that Coryneform bacteria produce pantothenic acid in an improved manner after attenuation of the poxB gene, which codes for pyruvate oxidase (EC 1.2.2.2).

"Isolated" means separated out of its natural environment.

"Polynucleotide" in general relates to polyribonucleotides and polydeoxyribonucleotides, it being possible for these to be non-modified RNA or DNA or modified RNA or DNA.

The nucleotide sequence of the poxB gene is shown in SEQ ID No. 1 and the resulting amino acid sequence of the enzyme protein is shown in SEQ ID No. 2.

The poxB gene described in SEQ ID No. 1 can be used according to the invention. Alleles of the poxB gene which result from the degeneracy of the genetic code or due to "sense mutations" of neutral function can further be used.

A new nucleotide sequence, shown in SEQ ID No. 6, which lies upstream of the nucleotide sequence of the poxB gene region shown in SEQ ID No. 1 has been found. A new nucleotide sequence, shown in SEQ ID No. 7, which lies downstream of the nucleotide sequence of the poxB gene region shown in SEQ ID No. 1 has further been found. The sequence of the poxB gene region shown in SEQ ID No. 4 has been obtained in this manner.

The poxB gene can also comprise a nucleotide sequence which hybridizes under stringent conditions to the above-nucleotide sequences. Suitable stringent conditions comprises washing in 5×SSC at a temperature of from 50 to 68° C.

It has been found that these polynucleotides shown in SEQ ID No. 6 and 7 are useful in the production of mutants with an attenuated, in particular eliminated, poxB gene.

It has also been found that Coryneform bacteria produce pantothenic acid in an improved manner after attenuation of the poxB gene.

To achieve an attenuation, either the expression of the poxB gene or the catalytic properties of the enzyme protein can be reduced or eliminated. The two measures can optionally be combined.

The decrease in gene expression can take place by suitable culturing or by genetic modification ("mutation") of the signal structures of gene expression. Signal structures of gene expression are, for example, repressor genes, activator genes, operators, promoters, attenuators, ribosome binding sites, the start codon and terminators. The expert can find information on this e.g. in the patent application WO 96/15246, in Boyd and Murphy (Journal of Bacteriology 170: 5949 (1988)), in Voskuil and Chambliss (Nucleic Acids Research 26: 3548 (1998), in Jensen and Hammer (Biotechnology and Bioengineering 58: 191 (1998)), in Patek et al. (Microbiology 142: 1297 (1999)) and in known textbooks of genetics and molecular biology, e.g. the textbook by Knippers ("Molekulare Genetik", 6th edition, Georg Thieme Verlag, Stuttgart, Germany, 1995) or that by Winnacker ("Gene und Klone", VCH Verlagsgesellschaft, Weinheim, Germany, 1990).

Mutations which lead to a change or reduction in the catalytic properties of enzyme proteins are known from the prior art. Examples which may be mentioned are the works of Qiu and Goodman (Journal of Biological Chemistry 272: 8611–8617 (1997)), Sugimoto et al. (Bioscience Biotechnology and Biochemistry 61: 1760–1762 (1997)) and M öckel ("Die Threonindehydratase aus *Corynebacterium glutamicum*: Aufhebung der allosterischen Regulation und Struktur des Enzyms", Reports from the Jülich Research Center, Jül-2906, ISSN09442952, Jülich, Germany, 1994). Summarizing descriptions can be found in known textbooks of genetics and molecular biology, e.g. that by Hagemann ("Allgemeine Genetik", Gustav Fisch Possible mutations are transitions, transversions, insertions and deletions. Depending on the effect of the amino acid exchange on the enzyme activity, "missense mutations" or "nonsense mutations" are referred to. Insertions or deletions of at least one base pair (bp) in a gene lead to "frame shift mutations", which lead to incorrect amino acids being incorporated or translation being interrupted prematurely.

Deletions of several codons typically lead to a complete loss of the enzyme activity. Instructions on generation of such mutations are prior art and can be found in known textbooks of genetics and molecular biology, e.g. the textbook by Knippers ("Molekulare Genetik", 6th edition, Georg Thieme Verlag, Stuttgart, Germany, 1995), that by Winnacker ("Gene und Klone", VCH Verlagsgesellschaft, Weinheim, Germany, 1990) or that by Hagemann ("Allgemeine Genetik", Gustav Fischer Verlag, Stuttgart, 1986).

An example of a plasmid with the aid of which an insertion mutagenesis of the poxB gen can be carried out is pCR2.1poxBint (FIG. 1).

Plasmid pCR2.1poxBint comprises the plasmid pCR2.1-TOPO described by Mead et al. (Bio/Technology 9:657–663 (1991)), into which an internal fragment of the poxB gene, shown in SEQ-ID No. 3 has been incorporated. After transformation and homologous recombination in the chromosomal poxB gene (insertion), this plasmid leads to a total loss of the enzyme function.

Figure 2:
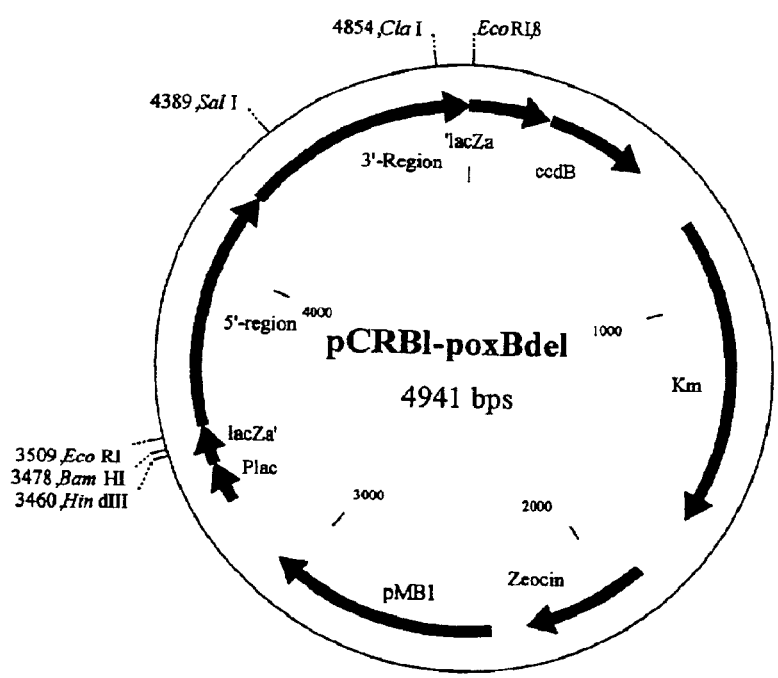
FIG. 2: Map of the plasmid pCR1-poxBdel.

Another example of a mutated poxB gene is the ΔpoxB allele contained in the plasmid pCRB1-poxBdel (FIG. 2). The ΔpoxB allele contains only the 5' and the 3' flank of the poxB gene. The 1737 bp long section of the coding region is missing (deletion). The nucleotide sequence of the ΔpoxB allele and of the 5' and 3' flank is shown in SEQ ID No. 12. This ΔpoxB allele can be incorporated into Coryneform bacteria by integration mutagenesis. The above-mentioned plasmid pCRB1-poxBdel is used for this, or the ΔpoxB allele is transferred to the plasmid pK18mobsacB and the plasmid of the type pK18mobsacBpoxBdel thereby formed is used. After transfer by conjugation or transformation and homologous recombination by means of a first "cross-over" event which effects integration and a second "cross-over" event which effects excision in the poxB gene, the incorporation of the ΔpoxB allele is achieved and a total loss of the enzyme function in the particular strain is achieved. The invention provides the ΔpoxB allele characterized by SEQ ID No. 12.

Further instructions and explanations on insertion mutagenesis or integration mutagenesis and gene replacement are to be found, for example, in Schwarzer and Pühler (Bio/Technology 9, 84–87 (1991)), Peters-Wendisch et al. (Microbiology 144, 915–927 (1998)) or Fitzpatrick et al. (Applied Microbiology and Biotechnology 42, 575–580 (1994)).

It may further be advantageous for the production of pantothenic acid, in addition to the attenuation of the gene which codes for pyruvate oxidase, for one or more of the genes chosen from the group consisting of the panB gene which codes for ketopantoate hydroxymethyl transferase (Sahm et al., Applied and Environmental Microbiology, 65, 1973–1979 (1999)), the panC gene which codes for pantothenate synthetase (Sahm et al., Applied and Environmental Microbiology, 65, 1973–1979 (1999)), the ilvC gene which codes for acetohydroxy-acid isomeroreductase (EMBL gene library: Accession No. L09232), and the ilvD gene which codes for dihydroxy-acid dehydratase (EP-A-1006189);

to be enhanced, in particular over-expressed.

The term "enhancement" in this connection describes the increase in the intracellular activity of one or more enzymes in a microorganism which are coded by the corresponding DNA, for example by increasing the number of copies of the gene or genes, using a potent promoter or using a gene which codes for a corresponding enzyme having a high activity, and optionally combining these measures.

By attenuation measures, the activity or concentration of the corresponding protein is in general reduced to 0 to 75%, 0 to 50%, 0 to 25%, 0 to 10% or 0 to 5% of the activity or concentration of the wild-type protein or of the activity or concentration of the protein in the starting microorganism.

It may further be advantageous for the production of pantothenic acid, in addition to the attenuation of the gene which codes for pyruvate oxidase, for the pck gene which codes for phosphoenol pyruvate carboxykinase (PEP carboxykinase) (DE: 19950409.1, DSM 13047) to be attenuated.

Finally, in addition to attenuation of pyruvate oxidase, it may be advantageous for the production of pantothenic acid to eliminate undesirable side reactions (Nakayama: "Breeding of Amino Acid Producing Micro-organisms", in: Overproduction of Microbial Products, Krumphanzl, Sikyta, Vanek (eds.), Academic Press, London, UK, 1982) which reduce the production of pantothenic acid.

The microorganisms prepared according to the invention can be cultured continuously or discontinuously in the batch process (batch culture) or in the fed batch (feed process) or repeated fed batch process (repetitive feed process) for the purpose of pantothenic acid production. A summary of known culture methods is described in the textbook by Chmiel (Bioprozesstechnik 1. Einführung in die Bioverfahrenstechnik (Gustav Fischer Verlag, Stuttgart, 1991)) or in the textbook by Storhas (Bioreaktoren und periphere Einrichtungen (Vieweg Verlag, Braunschweig/Wiesbaden, 1994)).

The culture medium to be used must meet the requirements of the particular microorganisms in a suitable manner. Descriptions of culture media for more various microorganisms are contained in the handbook "Manual of Methods for General Bacteriology" of the American Society for Bacteriology (Washington D.C., USA, 1981).

Sugars and carbohydrates, e.g. glucose, sucrose, lactose, fructose, maltose, molasses, starch and cellulose, oils and fats, e.g. soya oil, sunflower oil, groundnut oil and coconut fat, fatty acids, e.g. palmitic acid, stearic acid and linoleic acid, alcohols, e.g. glycerol and ethanol, and organic acids, e.g. acetic acid, can be used as the source of carbon. These substances can be used individually or as a mixture.

Organic nitrogen-containing compounds, such as peptones, yeast extract, meat extract, malt extract, corn steep liquor, soya bean flour and urea, or inorganic compounds, such as ammonium sulfate, ammonium chloride, ammonium phosphate, ammonium carbonate and ammonium nitrate, can be used as the source of nitrogen. The sources of nitrogen can be used individually or as a mixture.

Potassium dihydrogen phosphate or dipotassium hydrogen phosphate or the corresponding sodium-containing salts can be used as the source of phosphorus. The culture medium must further comprise salts of metals, e.g. magnesium sulfate or iron sulfate, which are necessary for growth. Finally, essential growth substances, such as amino acids and vitamins, can be employed in addition to the above-mentioned substances. Precursors of pantothenic acid, such as aspartate, β-alanine, ketoisovalerate, ketopantoic acid or pantoic acid, and optionally salts thereof, can moreover be added to the culture medium to additionally increase the pantothenic acid production. The starting substances mentioned can be added to the culture in the form of a single batch, or can be fed in during the culture in a suitable manner.

Basic compounds, such as sodium hydroxide, potassium hydroxide, ammonia, or acid compounds, such as phosphoric acid or sulfuric acid, can be employed in a suitable manner to control the pH of the culture. Antifoams, e.g. fatty acid polyglycol esters, can be employed to control the development of foam. Suitable substances having a selective action, e.g. antibiotics, can be added to the medium to maintain the stability of plasmids. To maintain aerobic conditions, oxygen or oxygen-containing gas mixtures, e.g. air, are introduced into the culture. The temperature of the culture is usually 20° C. to 45° C., and preferably 25° C. to 40° C. Culturing is continued until a maximum of pantothenic acid has formed. This target is usually reached within 10 hours to 160 hours.

The concentration of pantothenic acid formed can be determined with known chemical (Velisek; Chromatographic Science 60, 515–560 (1992)) or microbiological methods, e.g. the *Lactobacillus plantarum* test (DIFCO MANUAL, 10$^{th}$ Edition, p. 1100–1102; Michigan, USA).

The following microorganism was deposited on 19, Oct. 1999 as a pure culture at the Deutsche Sammlung für Mikroorganismen und Zellkulturen (DSMZ=German Collection of Microorganisms and Cell Cultures, Braunschweig, Germany) in accordance with the Budapest Treaty:

*Escherichia coli* strain DH5α/pCR2.1poxBint as DSM 13114.

Having generally described this invention, a further understanding can be obtained by reference to certain specific examples which are provided herein for purposes of illustration only, and are not intended to be limiting unless otherwise specified.

EXAMPLE 1
Preparation of a Genomic Cosmid Gene Library from *Corynebacterium glutamicum* ATCC 13032

Chromosomal DNA from *C. glutamicum* ATCC 13032 was isolated as described by Tauch et al. (1995, Plasmid 33:168–179) and partly cleaved with the restriction enzyme Sau3AI (Amersham Pharmacia, Freiburg, Germany, Product Description Sau3AI, Code no. 27-0913-02). The DNA fragments were dephosphorylated with shrimp alkaline phosphatase (Roche Molecular Biochemicals, Mannheim, Germany, Product Description SAP, Code no. 1758250). The DNA of the cosmid vector SuperCos1 (Wahl et al. (1987) Proceedings of the National Academy of Sciences USA 84:2160–2164), obtained from Stratagene (La Jolla, USA, Product Description SuperCos1 Cosmid Vector Kit, Code no. 251301) was cleaved with the restriction enzyme XbaI (Amersham Pharmacia, Freiburg, Germany, Product Description XbaI, Code no. 27-0948-02) and likewise dephosphorylated with shrimp alkaline phosphatase.

The cosmid DNA was then cleaved with the restriction enzyme BamHI (Amersham Pharmacia, Freiburg, Germany, Product Description PamHI, Code no. 27-0868-04). The cosmid DNA treated in this manner was mixed with the treated ATCC13032 DNA and the batch was treated with T4 DNA ligase (Amersham Pharmacia, Freiburg, Germany, Product Description T4-DNA-Ligase, Code no. 27-0870-04). The ligation mixture was then packed in phages with the aid of Gigapack II XL Packing Extract (Stratagene, La Jolla, USA, Product Description Gigapack II XL Packing Extract, Code no. 200217). For infection of the *E. coli* strain NM554 (Raleigh et al. 1988, Nucleic Acid Res. 16:1563–1575) the cells were taken up in 10 mM MgSO$_4$ and mixed with an aliquot of the phage suspension. The infection and titering of the cosmid library were carried out as described by Sambrook et al. (1989, Molecular Cloning: A Laboratory Manual, Cold Spring Harbor), the cells being plated out on LB agar (Lennox, 1955, Virology, 1:190) with 100 µg/ml ampicillin. After incubation overnight at 37° C., recombinant individual clones were selected.

EXAMPLE 2
Isolation and Sequencing of the poxB Gene

The cosmid DNA of an individual colony was isolated with the Qiaprep Spin Miniprep Kit (Product No. 27106, Qiagen, Hilden, Germany) in accordance with the manufacturer's instructions and partly cleaved with the restriction enzyme Sau3AI (Amersham Pharmacia, Freiburg, Germany, Product Description Sau3AI, Product No. 27-0913-02). The DNA fragments were dephosphorylated with shrimp alkaline phosphatase (Roche Molecular Biochemicals, Mannheim, Germany, Product Description SAP, Product No. 1758250). After separation by gel electrophoresis, the cosmid fragments in the size range of 1500 to 2000 bp were isolated with the QiaExII Gel Extraction Kit (Product No. 20021, Qiagen, Hilden, Germany).

The DNA of the sequencing vector pZero-1, obtained from Invitrogen (Groningen, The Netherlands, Product Description Zero Background Cloning Kit, Product No. K2500-01) was cleaved with the restriction enzyme BamHI (Amersham Pharmacia, Freiburg, Germany, Product Description BamHI, Product No. 27-0868-04). The ligation of the cosmid fragments in the sequencing vector pZero-1 was carried out as described by Sambrook et al. (1989, Molecular Cloning: A Laboratory Manual, Cold Spring Harbor), the DNA mixture being incubated overnight with T4 ligase (Pharmacia Biotech, Freiburg, Germany). This ligation mixture was then electroporated (Tauch et al., 1994, FEMS Microbiol Letters, 123:343–7) into the *E. coli* strain DH5αMCR (Grant, 1990, Proceedings of the National Academy of Sciences, U.S.A., 87:4645–4649) and plated out on LB agar (Lennox, 1955, Virology, 1:190) with 50 µg/ml zeocin.

The plasmid preparation of the recombinant clones was carried out with the Biorobot 9600 (Product No. 900200, Qiagen, Hilden, Germany). The sequencing was carried out by the dideoxy chain termination method of Sanger et al. (1977, Proceedings of the National Academies of Sciences, U.S.A., 74:5463–5467) with modifications according to Zimmermann et al. (1990, Nucleic Acids Research, 18:1067). The "RR dRhodamin Terminator Cycle Sequencing Kit" from PE Applied Biosystems (Product No. 403044, Weiterstadt, Germany) was used. The separation by gel electrophoresis and analysis of the sequencing reaction were carried out in a "Rotiphoresis NF Acrylamide/Bisacrylamide" Gel (29:1) (Product No. A124.1, Roth, Karlsruhe, Germany) with the "ABI Prism 377" sequencer from PE Applied Biosystems (Weiterstadt, Germany).

The raw sequence data obtained were then processed using the Staden program package (1986, Nucleic Acids Research, 14:217–231) version 97-0. The individual sequences of the pZero1 derivatives were assembled to a continuous contig. The computer-assisted coding region analyses were prepared with the XNIP program (Staden, 1986, Nucleic Acids Research, 14:217–231).

The resulting nucleotide sequence is shown in SEQ ID No. 1. Analysis of the nucleotide sequence showed an open reading frame of 1737 base pairs, which was called the poxB gene. The poxB gene codes for a polypeptide of 579 amino acids shown in SEQ ID No. 2.

EXAMPLE 3
Preparation of the Integration Vector pCR2.1poxBint for Mutagenesis of the poxB Gene From the strain ATCC 13032, chromosomal DNA was isolated by the method of Eikmanns et al. (Microbiology 140: 1817–1828 (1994)). On the basis of the sequence of the poxB gene known for *C. glutamicum* from Example 2, the following oligonucleotides were chosen for the polymerase chain reaction:

poxBint1:
5' TGC GAG ATG GTG AAT GGT GG 3'    (SEQ ID NO:13)

poxBint2:
5' GCA TGA GGC AAC GCA TTA GC 3'    (SEQ ID NO:14)

The primers shown were synthesized by MWG Biotech (Ebersberg, Germany) and the PCR reaction was carried out by the standard PCR method of Innis et al. (PCR Protocols. A Guide to Methods and Applications, 1990, Academic Press) with Pwo-Polymerase from Boehringer. With the aid of the polymerase chain reaction, a DNA fragment approx. 0.9 kb in size was isolated, this carrying an internal fragment of the poxB gene and being shown in SEQ ID No. 3.

The amplified DNA fragment was ligated with the TOPO TA Cloning Kit from Invitrogen Corporation (Carlsbad, Calif., USA; Catalogue Number K4500-01) in the vector pCR2.1-TOPO (Mead at al. (1991) Bio/Technology 9:657–663). The *E. coli* strain Top10F' (Grant et al. (1990) Proceedings of the National Academy of Sciences, USA, 87:4645–4649) was then electroporated. Selection for plasmid-carrying cells was made by plating out the transformation batch on LB agar (Sambrook et al., Molecular Cloning: A Laboratory Manual, $2^{nd}$ Ed., Cold Spring Harbor Laboratory Press, Cold Spring Harbor, N.Y., 1989), which had been supplemented with 50 mg/l kanamycin. Plasmid DNA was isolated from a transformant with the aid of the QIAprep Spin Miniprep Kit from Qiagen and checked by restriction with the restriction enzyme EcoRI and subsequent agarose gel electrophoresis (0.8%). The plasmid was called pCR2.1poxBint (FIG. 1).

EXAMPLE 4

Preparation of an Exchange Vector for Deletion Mutagenesis of the poxB Gene 4.1 Determination of the Nucleotide Sequence of the Flanks of the poxB Gene In further sequencing steps, the nucleotide sequence of the poxB gene region shown in SEQ ID No. 1 was extended upstream and downstream by in each case approx. 500 to 600 bp. The method described in Example 2 was used for this. The extended nucleotide sequence of the poxB gene region shown in SEQ ID No. 4 was obtained in this manner. The new nucleotide sequence upstream of the poxB gene region shown in SEQ ID No. 1 is shown in SEQ ID No. 6. The new nucleotide sequence downstream of the poxB gene region shown in SEQ ID No. 1 is shown in SEQ ID No. 7.

4.2 Construction of a ΔpoxB Allele

The method of geneSOEing-PCR described by Horton (Molecular Microbiology 3:93–99 (1995)) was used for construction of the ΔpoxB allele. The primer pairs shown in Table 1 (SEQ ID Nos. 8 to 11) were constructed for this. By means of a PCR, the 5' region before the poxB gene was amplified with primer pair 1 and the 3' region after the poxB gene was amplified with primer pair 2. A further PCR was then carried out with the two amplification products and the primers pox-del1 and pox-del4, as a result of which the two amplification products were joined by means of geneSOEing. The deletion fragment or ΔpoxB allele obtained in this way contains the flanking sequences of the poxB gene. The nucleotide sequence of the ΔpoxB allele is shown in SEQ ID No. 12.

TABLE 1

| Primer | 5'-Sequence-3' | | Primer pair |
|---|---|---|---|
| pox-del1 | ATGAGGAACATCCGGCGGTG | (SEQ ID NO:8) | 1 |
| pox-del2 | GAGAACAGCAGGAGTATCAATCATCA CTGAACTCCTCAACGTTATGGC | (SEQ ID NO:9) | |
| pox-del3 | TGATGATTGATACACCTGCTGTTCTC | (SEQ ID NO:10) | 2 |
| pox-del4 | TCATTGCCACCTGCTTCTCA | (SEQ ID NO:11) | |

4.3 Construction of an Exchange Vector

The DNA fragment obtained in this way was ligated with the Zero Blunt TOPO PCR Cloning Kit from Invitrogen Corporation (Carlsbad, Calif., USA; Catalogue Number K2800-20) in the pCR-Blunt II-TOPO vector (Shuman et al., (1994) Journal of Biological Chemistry 269:32678–32684; Bernard et al., (1983) Journal of Molecular Biology 234:534–541). The oli Stamm Top10 (Grant et al. (1990) Proceedings of the National Academy of Sciences, USA 87:4645–4649) was then transformed with the ligation batch. Selection for plasmid-carrying cells was made by plating out the transformation batch on LB agar (Sambrook et al., Molecular Cloning: A Laboratory Manual, $2^{nd}$ Ed., Cold Spring Harbor Laboratory Press, Cold Spring Harbor, N.Y.), which had been supplemented with 50 mg/l kanamycin. Plasmid DNA was isolated from a transformant with the aid of the QIAprep Spin Miniprep Kit from Qiagen and checked by restriction with the restriction enzyme EcoRI and subsequent agarose gel electrophoresis (0.8%). The plasmid was called pCRB1-poxBdel (FIG. 2).

The insert carrying the ΔpoxB allele was excised from this plasmid by means of EcoRI, isolated from the gel and ligated in the non-replicative integration vector pK18mobsacB, which was also cleaved with EcoRI (Schafer et al., Gene 145, 69–73 (1994)). The clonings were carried out in *E. coli* DH5αmcr (Grant et al., (1990) Proceedings of the National Academy of Sciences, USA, 87: 4645–4649) as the host. The resulting plasmid was called pK18mobsacB-poxBdel.

EXAMPLE 5

Mutagenesis of the poxB Gene in the Strain FERM BP-1763

The L-valine-producing strain *Brevibacterium lactofermentum* FERM BP-1763 is described in U.S. Pat. No. 5,188,948.

For deletion of the poxB gene, the integration plasmid pK18mobsacB-poxBdel was electroporated in the strain FERM BP-1763. After selection for kanamycin (25 μg/ml), individual clones in which the inactivation vector was present integrated in the genome were obtained. To allow excision of the vector, individual colonies were incubated in 50 ml liquid LB medium without antibiotics for 24 hours at 30° C. and 130 rpm and then smeared on to sucrose-containing containing suagar plates (LB with 15 g/l agar and 10% sucrose). Clones which had lost the vector content again by a second recombination event were obtained by this selection (Jäger et al. 1992, Journal of Bacteriology 174:5462–5465). To identify those clones which carried the ΔpoxB allele, a polymerase chain reaction was carried out with the primers pox-del1 and pox-del4 (Table 1 and SEQ ID No. 8 and 11). These primers amplify on the whole DNA of the starting strain FERM BP-1763 a fragment approx. 3150 bp in size, while on the DNA of poxB deletion mutants the primers amplified a shortened fragment 1422 bp in size. A deletion mutant identified in this way is consequently lacking a region of the poxB gene 1.7 kb in size.

A strain produced and tested in this manner was called FERM BP-1763ΔpoxB and employed for further studies.

EXAMPLE 6

Preparation of Pantothenic Acid 6.1 Production of the Strains

The plasmid pND-DBC2, which carries the panB, panC and panD genes of Corynebacterium glutamicum, is known from EP-A-1006192. The plasmid is deposited in the form of the strain ATCC13032/pND-DBC2 as DSM 12437 at the Deutsche Sammlung für Mikroorganismen und Zellkulturen (DSMZ=German Collection of Microorganisms and Cell Cultures, Braunschweig, Germany) in accordance with the Budapest Treaty.

The pantothenic acid-producing strains FERM BP-1763/pND-DBC2 and FERM BP-1763ΔpoxB were formed by transformation of the strains FERM BP-1763 and FERM BP-1763ΔpoxB with the plasmid pND-DBC2.

6.2 Preparation of Pantothenic Acid

In each case a sample of the strains Brevibacterium lactofermentum FERM BP-1763/pND-DBC2 and FERM BP-1763ΔpoxB/pND-DBC2 was smeared on to HHK agar.

HHK agar comprises brain-heart agar, which was obtained from Merck KgaA (Darmstadt, Germany) and supplemented with kanamycin. The composition of the HHK agar is shown in Table 2.

This agar plate culture was incubated for 17 hours at 30° C. and then kept in a refrigerator at +40° C. Selected individual colonies were then propagated further on the same medium. Cell material of a clone was removed from the HHK agar with an inoculating loop and transferred to 100 mL HHK broth contained in a shaking flask of 1000 mL total volume.

HHK broth comprises brain-heart medium, which was obtained from Merck KgaA (Darmstadt, Germany) and supplemented with glucose and kanamycin. The composition of the HHK broth is shown in Table 3.

TABLE 2

HHK agar

| Substance | Amount per liter |
| --- | --- |
| Brain-heart agar | 52.0 g |
| Kanamycin | 25 mg |

TABLE 3

HHK broth

| Substance | Amount per liter |
| --- | --- |
| Brain-heart medium | 37.0 g |
| Kanamycin | 25 mg |
| Glucose | 20.0 g |

The batches were incubated at 30° C. and 150 rpm for 22 hours. After the end of the culturing, an optical density of in each case approx. 6 was measured in a photometer at a wavelength of 660 nm (OD 660). This culture of the strain was used to inoculate the production fermenter.

Medium SK-71 shown in Table 4 was used for the fermentation. All the components of the SK-71 medium were initially introduced into the fermenter directly according to the working concentration and sterilized "in situ".

TABLE 4

Medium SK-71

| Compound | Amount per liter |
| --- | --- |
| Glucose hydrate | 110.0000 g |
| Corn steep liquor (CSL) | 5.0000 g |
| β-Alanine | 5.0000 g |
| Nicotinic acid | 0.0050 g |
| 1-Isoleucine | 0.1500 g |
| Homoserine | 0.1500 g |
| Ammonium sulfate | 25.0000 g |
| K dihydrogen phosphate | 0.1000 g |
| Mg sulfate 7H$_2$O | 1.0000 g |
| Fe sulfate 7H$_2$O | 0.0100 g |
| Mn sulfate H$_2$O | 0.0050 g |
| CaCl$_2$ * 2H$_2$O | 0.0100 g |
| Thiamine HCl | 0.0002 g |
| D(+)Biotin | 0.0003 g |
| Structol | 0.60 g |

10 l stirred reactors from B.Braun (BBI, Germany, Melsungen, Biostat E/ED model) were used as the fermenters.

For inoculation of 1950 g of the fermentation medium SK-71, in each case 100 mL of the shaking flask precultures in HHK broth described above were employed.

The batch was cultured over the entire fermentation time at a temperature of 30° C., a volume-specific aeration of 0.75 vvm, stirring, dependent on the oxygen consumption, of 800–1700 rpm and a pH of 7.0 and an oxygen partial pressure of 20% of the atmospheric saturation. The culture was cultured for a total of approx. 49 hours under the above-mentioned conditions until an OD660 of approx. 26 was reached. An aqueous ammonia solution (25% w/v) was used as the correcting agent for regulating the pH.

The optical density (OD) was then determined with a digital photometer of the type LP1W from Dr. Bruno Lange GmbH (Berlin, Germany) at a measurement wavelength of 660 nm and the concentration of D-pantothenic acid formed was determined by means of HPLC (Hypersil APS 2 5 μm, 250×5 mm, RI detection).

A D-pantothenic acid concentration of approx. 0.20 g/l was measured in the end sample (approx. 49 hours) of the fermentation culture of the strain FERM BP-1763/pND-DBC2.

The pantothenic acid concentration in the corresponding sample of the strain FERM BP-1763ΔpoxB/pND-DBC2 was approx. 0.23 g/l.

The base pair numbers stated are approx. values obtained in the context of reproducibility.

The abbreviations and designations used have the following meaning:

| | |
|---|---|
| ApR | Ampicillin resistance gene |
| ColE1 ori | Replication origin ColE1 |
| f1 ori | Replication origin of phage f1 |
| KmR | Kanamycin resistance gene |
| lacZ | Residues of the lacZα gene fragment |
| poxBint | Internal fragment of the poxB gene |
| 'lacZa | 3' end of the lacZα gene fragment |
| 3'-Region | 3' flank of the poxB gene |
| 5'-Region | 5' flank of the poxB gene |
| ccdB | ccdB gene |
| Km | Kanamycin resistance gene |
| lacZa' | 5' end of the lacZα gene fragment |
| plac | Promoter of the lac operon |
| pMB1 | Replication origin of the plasrnid pMB1 |
| Zeocin | Zeocin resistance gene |

The following abbreviations have moreover been used:

| | |
|---|---|
| BamHI: | Cleavage site of the restriction enzyme BamHI |
| ClaI | Cleavage site of the restriction enzyme ClaI |
| EcoRI: | Cleavage site of the restriction enzyme EcoRI |
| HindIII: | Cleavage site of the restriction enzyme HindIII |
| SalI: | Cleavage site of the restriction enzyme SalI |

Obviously, numerous modifications and variations on the present invention are possible in light of the above teachings. It is therefore to be understood that within the scope of the appended claims, the invention may be practiced otherwise than as specifically described herein.

What is claimed is:

1. A process for preparing D-pantothenic acid and/or a salt thereof, comprising:

culturing a recombinant modified Coryneform bacterium for a time and under conditions suitable for producing D-pantothenic acid or a salt thereof, and collecting the D-pantothenic acid or a salt thereof;

wherein the pox B gene is deleted in the recombinant modified Coryneform bacterium, wherein the poxB gene in the Coryneform bacterium prior to being deleted comprises SEQ ID NO:1, SEQ ID NO:4, a polynucleotide which hybridizes under stringent conditions to the full complement of SEQ ID NO:1 and which encodes a protein with pyruvate oxidase activity, or a polynucleotide which hybridizes under stringent conditions to the full complement of SEQ ID NO:4 and which encodes a protein with pyruvate oxidase activity, wherein the stringent conditions comprise washing in 5×SSC at a temperature of 68° C.

2. The process of claim 1, wherein the D-pantothenic acid is concentrated prior to said collecting.

3. The process of claim 1, wherein the D-pantothenic acid is concentrated after said collecting.

4. The process of claim 1, further comprising purifying the D-pantothenic acid and/or a D-pantothenic salt.

5. The process of claim 1, wherein said recombinant modified Coryneform bacteria is *Corynebacterium glutamicum*.

6. The process of claim 1, wherein said recombinant modified Coryneform bacterium is selected from the group consisting of *Corynebacterium acteoglutamicum, Corynebacterium acetoacidophilum, Corynebacterium thermoaminogenes, Brevibacterium flavum, Brevibacterium lactofermentum*, and *Brevibacterium divaricatum*.

7. The process of claim 1, wherein said recombinant modified Coryneform bacterium further comprises one or more of genes overexpressed with a strong promoter, wherein the one or more genes are selected from the group consisting of panB which codes for ketopantoate hydroxymethyl transferase, panC which codes for pantothenate synthetase, ilvC which codes for acetohydroxy-acid isomeroreductase, and ilvD which codes for dihyroxy-acid dehydratase.

8. The process of claim 1, wherein the culturing is in a batch process.

9. The process of claim 1, wherein the culturing is in a fed batch process.

10. The process of claim 1, wherein the culturing is in a repeated fed batch process.

11. The process of claim 1, wherein said poxB gene in the Coryneform bacterium prior to being deleted comprises a polynucleotide which hybridizes under stringent conditions the full complement of SEQ ID NO:1 wherein said stringent conditions comprise washing in 5×SSC at a temperature 68° C.

12. The process of claim 1, wherein said poxB gene in the Coryneform bacterium prior to being deleted comprises SEQ ID NO:1.

13. The process of claim 1, wherein said poxB gene in the Coryneform bacterium prior to being deleted comprises SEQ ID NO:4.

14. The process of claim 1, wherein said poxB gene in the Coryneform bacterium prior to being deleted comprises a polynucleotide which hybridizes under stringent conditions to the full complement of SEQ ID NO:4, wherein said stringent conditions comprise washing in 5×SSC at a temperature of 68° C.

15. The process of claim 1, wherein said poxB gene in the Coryneform bacterium prior to being deleted comprises a polynucleotide encoding a protein comprising the amino acid sequence of SEQ ID NO:2.

* * * * *